(12) United States Patent
Buerger et al.

(10) Patent No.: US 11,270,436 B2
(45) Date of Patent: Mar. 8, 2022

(54) TISSUE CLASSIFICATION USING IMAGE INTENSITIES AND ANATOMICAL POSITIONS

(71) Applicant: KONINKLIJKE PHILIPS N.V., Eindhoven (NL)

(72) Inventors: Christian Buerger, Hamburg (DE); Steffen Renisch, Hamburg (DE)

(*) Notice: Subject to any disclaimer, the term of this patent is extended or adjusted under 35 U.S.C. 154(b) by 0 days.

(21) Appl. No.: 16/961,706

(22) PCT Filed: Jan. 9, 2019

(86) PCT No.: PCT/EP2019/050358
§ 371 (c)(1),
(2) Date: Jul. 13, 2020

(87) PCT Pub. No.: WO2019/141543
PCT Pub. Date: Jul. 25, 2019

(65) Prior Publication Data
US 2021/0150714 A1 May 20, 2021

(30) Foreign Application Priority Data
Jan. 16, 2018 (EP) .................................. 18151866

(51) Int. Cl.
*G06K 9/00* (2006.01)
*G06T 7/00* (2017.01)
(Continued)

(52) U.S. Cl.
CPC ........ *G06T 7/0014* (2013.01); *G01R 33/4828* (2013.01); *G01R 33/5608* (2013.01);
(Continued)

(58) Field of Classification Search
CPC ......... G06T 7/0014; G06T 2207/10088; G06T 2207/20081; G06T 2207/30004;
(Continued)

(56) References Cited

U.S. PATENT DOCUMENTS 9,280,819 B2 * 3/2016 Codella .................. G06K 9/621
9,474,495 B2 * 10/2016 Ahn ...................... A61B 6/4417
(Continued)

OTHER PUBLICATIONS

Powell et al "Registration and machine learning-based automated segmentation of subcortical and cerebellar brain structures", Neuroimage, Elsevier, Amsterdam, NL,vol. 39, No. 1,Jan. 1, 2008 (Jan. 1, 2008), pp. 238-247 (Year: 2008).*
(Continued)

*Primary Examiner* — Van D Huynh

(57) ABSTRACT

The invention relates to a medical image data processing system (101) for image segmentation. The medical image data processing system (101) comprises a machine learning framework trained to receive an anatomical position of a voxel and to provide a tissue type classification. An execution of machine executable instructions by a processor (130) of the medical image data processing system (101) causes the processor (130) to control the medical image data processing system (101) to: —receive medical image data (140) comprising an anatomical structure of interest, —fit an anatomical frame of reference (302, 402) to the medical image data (140) using model-based segmentation, —classify tissue types represented by voxels of the medical image data (140) using the machine learning framework, wherein anatomical positions of the voxels with respect to the anatomical frame of reference (302, 402) are used as the input to the machine learning framework.

12 Claims, 7 Drawing Sheets

(51) Int. Cl.
*G16H 30/40* (2018.01)
*G01R 33/48* (2006.01)
*G01R 33/56* (2006.01)
*G06K 9/62* (2022.01)

(52) U.S. Cl.
CPC ......... *G06K 9/6256* (2013.01); *G06K 9/6262* (2013.01); *G16H 30/40* (2018.01); *G06K 2209/05* (2013.01); *G06T 2207/10088* (2013.01); *G06T 2207/20081* (2013.01); *G06T 2207/30004* (2013.01)

(58) Field of Classification Search
CPC ............. G06T 7/12; G06T 2207/10081; G06T 2207/20084; G06T 2207/30016; G06T 7/0012; G16H 30/40; G01R 33/4828; G01R 33/5608; G06K 9/6256; G06K 9/6262; G06K 2209/05; G06K 9/32
USPC .......................................................... 382/131
See application file for complete search history.

(56) References Cited

U.S. PATENT DOCUMENTS

| | | | |
|---|---|---|---|
| 10,029,121 B2 * | 7/2018 | Li | A61N 5/1038 |
| 2009/0226060 A1 * | 9/2009 | Gering | G06T 7/11 382/128 |
| 2016/0098621 A1 * | 4/2016 | Tahmasebi Maraghoosh | A61B 5/055 600/411 |
| 2017/0072222 A1 * | 3/2017 | Siversson | G06T 7/337 |
| 2018/0182101 A1 * | 6/2018 | Petersen | G06T 7/13 |
| 2018/0360313 A1 * | 12/2018 | Zhang | G06T 7/33 |

OTHER PUBLICATIONS

Hofmann, Matthias, et al. "MRI-based attenuation correction for PET/MRI: a novel approach combining pattern recognition and atlas registration." Journal of nuclear medicine 49.11 (2008): 1875-1883.

Xiang et al "Deep Embedding Convolutional Neural Network for Synthesizing CT Image From T1-Weighted MR Image" Medical Image Analysis vol. 47, Jul. 2018, p. 31-44.

Htynh et al "Estimating CT Image From MRI Data Using Structured Random Forest and Auto Context Model" IEEE Trans Med Imaging. Jan. 2016 ; 35(1): 174-183. doi:10.1109/TMI.2015.2461533.

International Search Report and Written Opinion from PCT/EP2019/050358 dated Feb. 19, 2019.

Powell et al "Registration and machine learning-based automated segmentation of subcortical and cerebellar brain structures",NEUR0IMAGE, Elsevier, Amsterdam, NL,vol. 39, No. 1,Jan. 1, 2008 (Jan. 1, 2008), pp. 238-247.

Eun Young Kim et al: "Multi-structure segmentation of multi-modal brain images using artificial neural networks",Proceedings Optical Diagnostics of Living Cells II,vol. 7623, Mar. 4, 2010 (Mar. 4, 2010), p. 76234B.

Petronella Anbeek et al: "Probabilistic Brain Tissue Segmentation in Neonatal Magnetic Resonance Imaging", Pediatric Research,vol. 63, No. 2,Feb. 1, 2008 (Feb. 1, 2008), pp. 158-163.

Teresa Wu et al: "A prior feature SVM-MRF based method for mouse brain segmentation",Neuroimage, Elsevier, Amsterdam, NL,vol. 59, No. 3, Sep. 22, 2011 (Sep. 22, 2011), pp. 2298-2306.

* cited by examiner

TISSUE CLASSIFICATION USING IMAGE INTENSITIES AND ANATOMICAL POSITIONS

CROSS REFERENCE TO RELATED APPLICATIONS

This application is a U.S. national phase application of International Application No. PCT/EP2019/050358 filed on Jan. 9, 2019, which claims the benefit of EP Application Serial No. 18151866.3 filed on Jan. 16, 2018 and is incorporated herein by reference.

FIELD OF THE INVENTION

The invention relates to processing medical image data, in particular it relates to methods and apparatuses for classifying tissue types using medical image data.

BACKGROUND OF THE INVENTION

For the usage of medical image data, image segmentation and classification of voxels comprised by image data are an important but challenging task in order to identify and analyze anatomical structures of interest.

In order to analyze an anatomical structure of interest, not only its boundary contours, but also its internal structure may be important. It may in particular be important to determine which tissue types are comprised by the respective anatomical structure. Model-based segmentation using shape models have proven robust and successful in segmenting organs from medical images with high accuracy. Using model-based segmentation, certain areas within an image are delineated and labeled. However, such model-based segmentation may be unable to determine internal structural information of the segmented area, since only the boundaries are modeled. In other words, model-based segmentation only provides the anatomical positions at the organ boundaries but the anatomical positions over the complete image volume required for 3D tissue classification cannot be provided.

SUMMARY OF THE INVENTION

The invention provides for a medical image data processing system, a method of operating the medical image data processing system, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator. A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance Imaging (MRI) data, also referred to as Magnetic Resonance (MR) data or magnetic resonance image data, is defined herein as being the recorded measurements of radio frequency signals emitted by nuclear spins using the antenna of a magnetic resonance apparatus during a magnetic resonance imaging scan. Magnetic resonance image data is an example of medical image data. A Magnetic Resonance Imaging (MRI) image or MR image is defined herein as being the reconstructed two or three-dimensional visualization of anatomic data comprised by the magnetic resonance imaging data, i.e. MRI images are provided by MRI data sets comprising a representative selection MRI data. This visualization can be performed using a computer. Magnetic resonance imaging data may be provided using a representation of the respective data in k-space or image space. Using a Fourier transformation, the magnetic resonance imaging data may be transformed from k-space to image space or vice versa. In the following, magnetic resonance image data may comprise a selection of MRI data in image space representative of a two or three-dimensional anatomic structure, i.e. an MRI image.

An 'anatomical structure' is any structure of the anatomy of a subject, like for example a person or an animal. A structure may comprise a certain organ like the liver or the brain, or a part of the same or it may comprise a certain anatomical area like the spine area, a knee, a shoulder etc.

'Segmentation' refers to a partitioning a digital image data into multiple segments, e.g. sets of pixels or voxels, in order to identify one or more segments, which represent structures of interest which may be further analyzed. Segmentation may be used to identify and locate structures, in particular their boundaries in the image data. For example, lines, curves, planes, surfaces etc. may be identified. Labels may be assigned to each pixel or voxel in an image such that pixels/voxels with the same label share certain characteristics and may be highlighted in order to indicate contours, areas or volumes comprised structures of interest. When applied to three-dimensional image data, e.g. a stack of two-dimensional images, the resulting contours after image segmentation may be used to create three dimensional reconstructions of shapes of structures of interest, like e.g. anatomical structures, with the help of interpolation algorithms like e.g. marching cubes. Three-dimensional contours may e.g. be provided by a surface mesh. The mesh may comprise a plurality of flat, two-dimensional polygons, like e.g. triangles.

'Model-based segmentation' refers to a segmentation using a shape model, e.g. in form of a surface mesh, which is deformed in order to be aligned with the boundaries of an anatomical structure of interest and to identify its contours.

The term 'machine learning' (ML) refers to a computer algorithm used to extract useful information from training data sets by building probabilistic frameworks, referred to as machine learning frameworks (also referred to as machine learning models), in an automated way. The machine learning may be performed using one or more learning algorithms such as linear regression, K-means, classification algorithm, reinforcement algorithm etc. A 'machine learning framework' may for example be an equation or set of rules that makes it possible to predict an unmeasured value (e.g. which tag corresponds to a given token) from other, known values and/or to predict or select an action to maximize a future reward. According to one embodiment, the machine learning framework is a deep learning framework.

For example, the learning algorithm may comprise classification and/or reinforcement algorithms. The reinforcement algorithm may for example be configured to learn one or more policies or rules for determining a next set of parameters (action) based on the current set of parameters and/or previously used set of parameters. For example, starting from the current set of parameters and/or previous set of acquisition parameters the machine learning framework may follow a policy until it reaches a desired set of acquisition parameters. The policy represents the decision-making process of the model at each step e.g. it defines which parameter to change and how to change it, which new parameter to add to the set of parameters etc. The selection of the actions may be optimized by learning based on known landmarks marked on input images.

'Image intensity' refers to the signal intensity comprised by individual voxels of the medical image data.

A 'anatomical frame of reference' refers to a frame of reference, e.g. a coordinate system, which defines positions relative to an anatomical reference structure. The anatomical frame of reference defines a reference space in which the anatomical reference structure is located. When the spatial form of the anatomical reference structure is deformed, the anatomical frame of reference is deformed accordingly.

In one aspect, the invention relates to a medical image data processing system. The medical image data processing system comprises a memory storing machine executable instructions and a machine learning model. The machine learning model is trained to receive an image intensity and an anatomical position of a voxel as an input and to provide a tissue type classification of the voxel in response as an output. The medical image data processing system further comprises a processor for controlling the medical image data processing system. An execution of the machine executable instructions by the processor causes the processor to control the medical image data processing system to receive medical image data comprising an anatomical structure of interest.

An anatomical frame of reference is fitted to the medical image data using model-based segmentation, wherein a model used for the model-based segmentation comprises an anatomical reference structure in a reference space defined by the anatomical frame of reference. Tissue types represented by voxels of the medical image data are classified using the machine learning framework. Each voxel comprises an image intensity. Image intensities of the voxels and anatomical positions of the voxels with respect to the anatomical frame of reference are used as the input to the machine learning framework.

Automated image segmentation may be desired in various medical imaging applications. For example, model-based segmentation using shape models, may provide a robust and accurate approach to segment anatomical structures of interest. However, such an approach may be unable to determine internal structures comprised by the segmented area, since only boundaries are modeled. Thus model-based segmentation may fail, when highly accurate voxel-wise volumetric classifications are desired. On the other hand, ML approaches, which attempt to classify each image voxel, may have the capability to deliver volumetric classification results with relatively little training effort. In other words, ML approaches may be able to take into account internal structure neglected by model-based segmentation. However, ML approaches generally rely on image features by the voxels to be classified. Such internal structures may comprise different tissue types showing similar or even identical image features, like e.g. intensities. ML approaches based on the images features of the structures to be analyzed as an input may fail, when different anatomical structures show similar image features. Consequently, such anatomical structures cannot be differentiated into separate classification classes. Known ML approaches may rather lack in regularizing properties of shape models and may require extensive post-processing.

Embodiments suggest to additionally take into account spatial relation of the underlying anatomy in order to be able to differentiate tissue types showing similar or even identical image features. Thus, the common model-based segmentation approach is extended by spatial encoding (SE) which provides a volumetric coordinate system with respect to an anatomical frame of reference, i.e. spatial information for each voxel.

According to embodiments, a combination of ML and SE may be used to overcome both methodological downsides. A shape model may be applied to implement an anatomical frame of reference for a medical image, i.e. a spatial reference frame which provides spatial coordinates relative to the anatomical reference structure represented by the shape model. Anatomical positions with respect to the anatomical frame of reference are is used as an additional input for ML besides on image features, like image intensity. Embodiments may allow to accurately classify target structures on a voxel-wise basis, while efficiently differentiating even different types of tissue with similar image features. In case of similar and/or identical identities the anatomical position may be used for differentiation. Thus, even internal structures may be imposed to segmented image areas.

According to embodiments, only such voxels may be classified by ML using their anatomical position for which it is known that image features provided by the same are ambiguous regarding the represented tissue type. Considering e.g. MR images, voxels representing air have similar image features as voxels representing bone. Both are dark, i.e. comprise a low intensity.

According to embodiments, only such voxels may be classified by ML using their anatomical position which comprise an image intensity above a predefined threshold, below a predefined threshold and/or within a range defined by a lower and an upper threshold. According to embodiments, all voxels are classified by ML using their anatomical position in addition to image features, like image intensity.

Embodiments may comprise a first step in which an anatomical frame of reference is fitted to an image. The anatomical frame of reference and an associated anatomical reference structure are provided prior to the segmentation of the anatomical structure of interest. An anatomical frame of reference may define coordinates relative to the anatomical reference structure. For example, a medical image is segmented using a surface model representing a target outline of the anatomical structure of interest. For this purpose, the surface model, i.e. an anatomical reference structure, is fitted to the anatomical structure of interest. The fitting may require a deformation of the respective model which is accompanied by a deformation of the anatomical frame of reference the form of which is fixed to the anatomical reference structure. In a second step, voxel-wise coordinates of the deformed anatomical frame of reference may be used as an additional input for ML. In other words, the generic classification features of ML are extended by the spatial position of each voxel depending on the form of the anatomical structure of interest, i.e. by the information where each voxel is positioned with respect to the underlying anatomy.

Embodiments may provide a method comprising the following steps:

Adding an anatomical frame of reference to an image using SE. The anatomical frame of reference may be added to the image e.g. by using model-based segmentation. For example, a skull model may be applied to an MR image of a head to segment the outline of the anatomical structure of interest. The anatomical frame of reference is deformed around the segmentation model to align with the respective MR image, e.g. using the mesh point correspondences from the skull model to the segmented outline followed by 3D interpolation schemes (B-splines, multilevel B-splines, Thin-plate, or other).

ML may be performed including the spatial encoding based on the anatomical positions. In addition to the voxel-wise image intensities of the MR image, e.g. the x/y/z coordinate of the deformed anatomical frame of reference are used as additional features in training and segmentation. Embodiments may allow to separate similarly appearing image voxels into separate classification classes. For instance, if a voxel of the MR image is dark and located inside of the yaw, ML may learn that it most probably is a cortical bone voxel. On the other hand, if a voxel of the MR image is dark and located within the nasal cavities, ML may learn that it is most probably an air voxel. Hence, SE may allow to separate the tissues which appear similar in MRI.

According to embodiments, both the SE as well as the ML may be implemented in various ways, e.g. using the normalized triangle coordinates or the distance to the closest triangle of the shape model along with its index, for instance using distance maps. Regarding, the ML any suitable classification method, like e.g. Random Forests, Support Vector Machines, Neural Networks, etc. may be used.

According to embodiments, training sets for multiple ones of medical image data samples of an anatomical structure of interest are received. The training set comprises for a respective one of the medical image data samples data identifying for each of the voxels an image intensity and a tissue type. A learning algorithm is executed on the training sets for generating the machine learning model framework. The training comprises determining for voxels of the medical image data samples an anatomical position of reference with respect to an anatomical frame of reference fitted to the medical image data sample. Thus, the machine learning model framework learns to identify the respective tissue types of the voxels based on the image intensity provided by the medical image data sample and the anatomical position determined for the respective voxels.

According to embodiments, the medical image data comprises magnetic resonance image data.

According to embodiments, the execution of the machine executable instructions further causes the processor to generate a pseudo-CT image using the magnetic resonance image data and the classification result.

Pseudo Computer Tomography (CT) images, also referred to as synthetic or virtual CT images, are simulated CT images calculated using data from one or more other medical imaging modalities. Pseudo-CT images may e.g. be calculated MRI data. For example a tissue classification according to embodiments may be applied to each of the voxels. For example, the magnetic resonance imaging tissue classifier may work by determining an average or a mean value of the voxels within a particular region. These may be normalized or scaled and then compared to a standard to identify a tissue type and assign a tissue classification. In case of ambiguities, the anatomical position may be taken into account as an additional input.

For example, a Hounsfield unit map may be calculated for the MRI image by assigning a Hounsfield unit value to each of the voxels according to the tissue classification. The Hounsfield mapping comprises a mapping between the tissue classification to Hounsfield units. Using the Hounsfield unit mapping, a pseudo-CT image may be calculated.

Embodiments may e.g. be used for MR-only radiotherapy application: A Pseudo-CT image may be generated from a given MR image by classifying each voxel of the MR image into different tissue classes, such as e.g. air, soft tissue and cortical bone. The resulting Pseudo-CT image may be intended to be used for dose planning. Most challenging is the separation of cortical bone and air, because they both appear dark in MR and cannot be distinguished on a pure intensity basis. SE may be applied to detect the head including air cavities and cortical bone tissue e.g. using model-based segmentation or atlas-bases registration. However, the highly variable and complex shape of bone and adjacent air tissue areas, such as the air-filled nasal cavities, can hardly be modeled accurately. Furthermore, a volumetric voxel-wise classification using common ML approaches may not be able to distinguish between air and bone voxels which are of a highly similar appearance.

Thus, embodiments may be of particular interest for MR-only radiotherapy (RT) applications. An incorporation of spatial information according to embodiments may allow such separation and hence a generation of appropriate Pseudo-CT images. Thus, embodiments may combine a robust shape-based segmentation approach with a data-driven ML approach, which in combination may drastically reduce the development and maintenance effort required. For example, different internal bone structures of different patient populations may share the same anatomical model, while differently trained classifiers may be used, which only require representative training data.

According to embodiments, the fitting of the anatomical frame of reference comprises deforming the respective frame together with the anatomical reference structure to align the deformed anatomical reference structure with the anatomical structure of interest.

According to embodiments, the model used for the model-based segmentation comprises a surface mesh used for the segmentation.

According to embodiments, the model comprises the anatomical frame of reference in form of a spatial reference frame of the surface mesh and wherein the model-based segmentation comprises deforming the anatomical frame of reference together with the surface mesh.

According to embodiments, at least two voxels with identical image intensities are assigned to different classes representing different tissue types based on different anatomical positions of the voxels with respect to the anatomical frame of reference.

According to embodiments, a first one of the different classes represents bone and a second one of the different classes represents air.

According to embodiments, the receiving of the medical image data comprises: sending a request for the respective medical image data to a database comprising the medical image data, wherein in response to the request the requested medical image data is received from the database.

According to embodiments, the medical image data processing system further comprises a magnetic resonance imaging system and wherein the magnetic resonance imaging system comprises:

a main magnet for generating a main magnetic field within an imaging zone, a magnetic field gradient system for generating a spatially dependent gradient magnetic field within the imaging zone, a radio-frequency antenna system configured for acquiring magnetic resonance data from the imaging zone, wherein the memory further stores pulse sequence commands, wherein the pulse sequence commands are configured for controlling the magnetic resonance imaging system to acquire the magnetic resonance data from the imaging zone, wherein the receiving of the medical image data comprises the execution of the machine executable instructions using pulse sequence commands and acquire the medical image data in form of magnetic resonance image data from the imaging zone by the radio-frequency antenna system.

In another aspect, the invention relates to a method for controlling a medical image data processing system. The medical image data processing system comprises a memory storing machine executable instructions and a machine learning framework. The machine learning framework is trained to receive an image intensity and an anatomical position of a voxel as an input and to provide a tissue type classification of the voxel in response as an output. The medical image data processing system further comprises a processor for controlling the medical image data processing system, wherein execution of the machine executable instructions by the processor causes the processor to control the medical image data processing system to execute the method. The method comprises receiving medical image data comprising an anatomical structure of interest. An anatomical frame of reference is fitted to the medical image data using model-based segmentation, wherein a model used for the model-based segmentation comprises an anatomical reference structure in a reference space defined by the anatomical frame of reference. Tissue-types represented by voxels of the medical image data are classified using the machine learning framework. Each voxel comprises an image intensity. Anatomical positions of the voxels with respect to the anatomical frame of reference are used as the input to the machine learning framework.

According to embodiments, the medical image data processing system further comprises a magnetic resonance imaging system and wherein the magnetic resonance imaging system comprises:

a main magnet for generating a main magnetic field within an imaging zone, a magnetic field gradient system for generating a spatially dependent gradient magnetic field within the imaging zone, a radio-frequency antenna system configured for acquiring magnetic resonance data from the imaging zone, wherein the memory further stores pulse sequence commands, wherein the pulse sequence commands are configured for controlling the magnetic resonance imaging system to acquire the magnetic resonance data from the imaging zone, wherein the receiving of the medical image data comprises the execution of the machine executable instructions using pulse sequence commands and acquire the medical image data in form of magnetic resonance image data from the imaging zone by the radio-frequency antenna system.

In another aspect, the invention relates to a computer program product for controlling a medical image data processing system comprising machine executable instructions for execution by a processor controlling the medical image processing system. The medical image data processing system comprises a memory storing a machine learning framework trained to receive an image intensity and an anatomical position of a voxel as an input and to provide a tissue type classification of the voxel in response as an output. The medical image data processing system further comprises a processor for controlling the medical image data processing system. An execution of the machine executable instructions by the processor causes the processor to control the medical image data processing system to receive medical image data comprising an anatomical structure of interest. An anatomical frame of reference is fitted to the medical image data using model-based segmentation, wherein a model used for the model-based segmentation comprises an anatomical reference structure in a reference space defined by the anatomical frame of reference, and tissue-types represented by voxels of the medical image data are classified using a machine learning framework. Each voxel comprises an image intensity. Images intensities of the voxels and anatomical positions of the voxels with respect to the anatomical frame of reference are used as the input to the machine learning framework.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
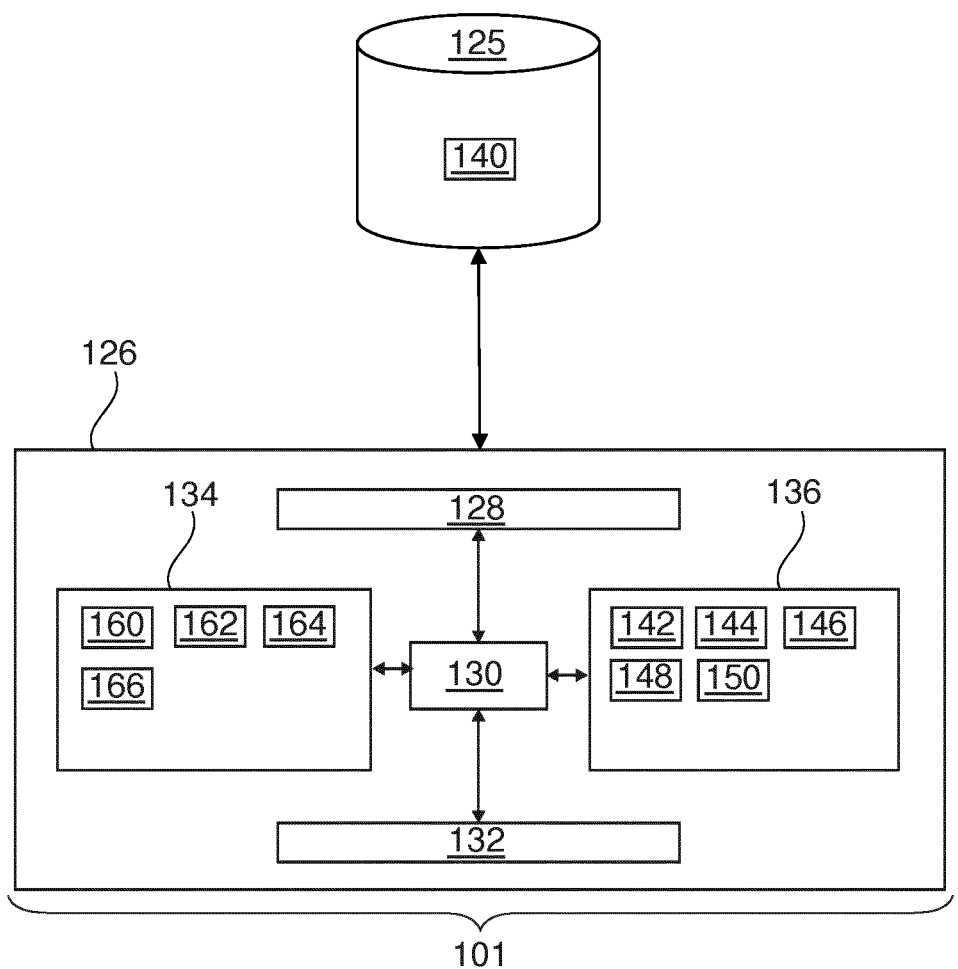
FIG. 1 illustrates an example of a medical image data processing system.

FIG. 1 shows an example of a medical image data processing system 101 comprising a computer 126. The computer 126 is shown as containing a processor 130 which is operable for executing machine-readable instructions. The computer 126 is further shown as comprising a user interface 132, computer storage 134 and computer memory 136 which are all accessible and connected to the processor 130. Furthermore, the computer 126 may communicatively be connected with a database 125. The computer 126 may be configured for requesting data, like medical image data 140 from the database 125 via the communication interface 128. According to embodiments, the database 125 may be provided by an external system and accessible for the computer 126 via a communication network using a communication connection. The communication connection may be established wireless or via a wire. According to embodiments the database 125 may be comprised by the computer 126 itself. For example, the database 125 may be comprised by the computer storage 134. According to further embodiments, the database 125 may be provided by a computer-readable storage medium. The database 125 contains imaging data 140. According to alternative embodiments, the computer storage 134 may provide the medical image data 140.

The computer 126 may be configured as a medical image data processing system 101. The computer memory 136 is shown as containing a control module 142. The control module 142 contains computer, i.e. machine, executable code or instructions which enable the processor 130 to control the operation and function of the medical image data processing system 101. The computer system 126 is e.g. controlled by the control module 142 to receive medical image data 140 for processing. The processing may comprise fitting an anatomical frame based on a segmentation and classifying tissue types of voxels.

For the processing of the medical image data 140, the computer memory 136 may further contain a segmentation module 144. The segmentation module 144 contains computer executable code or instructions which enable the processor 130 to perform a model-based segmentation of the medical image data 140. The result of the segmentation 160 comprises segmented medical image data which e.g. is stored in the computer storage 134.

The computer memory 136 may further contain a fitting module 146. The fitting module 146 contains computer executable code or instructions which enable the processor 130 to fit an anatomical frame of reference to the segmented medical image data 160. The resulting special encoded medical image data 162 may e.g. be stored in the computer storage 134.

The computer memory 136 may further contain a machine learning module 148. The machine learning module 148 contains computer executable code or instructions which enable the processor 130 to implement and execute a machine learning framework. The machine learning framework is trained to receive an image intensity and an anatomical position of a voxel as an input and to provide a tissue type classification of the voxel in response as an output. The output 164 machine learning module 148 may e.g. be stored in the computer storage 134.

The result of the classification 164 may e.g. be used by a transformation module 150. The transformation module 150 contains computer executable code or instructions which enable the processor 130 to transform MRI image data to pseudo-CT image data. The resulting pseudo-CT images 166 may e.g. be stored in the computer storage 134.

Figure 2:
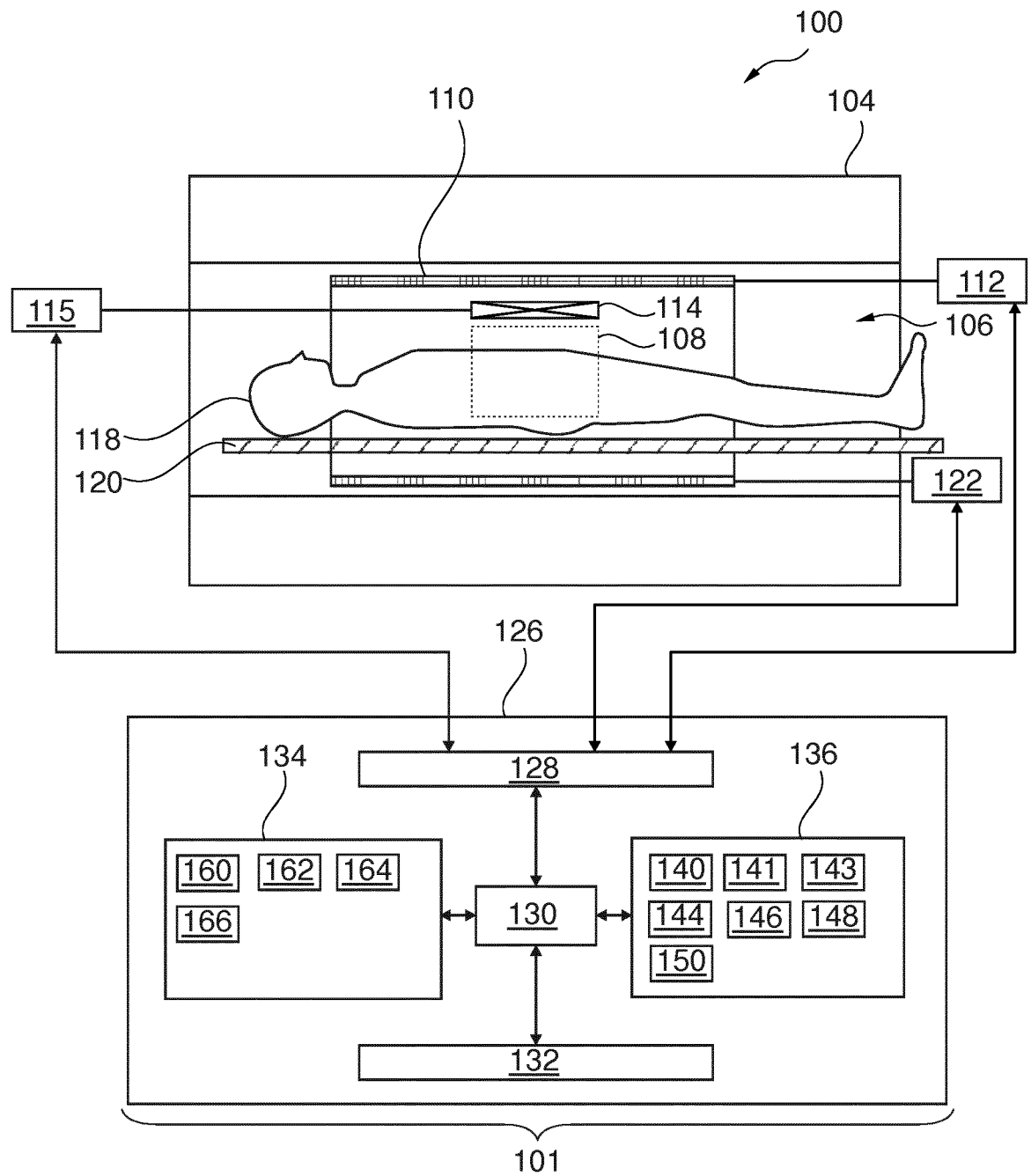
FIG. 2 illustrates an example of a magnetic resonance imaging system.

FIG. 2 shows an example of a medical image data processing system 101 comprising a magnetic resonance imaging system 100 with a magnet 104. The main magnet 104 is a superconducting cylindrical type magnet 104 with a bore 106 through it. The use of different types of magnets is also possible. For instance, it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 forming a magnetic field gradient system which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114, also referred to as radio-frequency antenna system, for manipulating the orientations of magnetic spins within the imaging zone 108 and for receiving radio transmissions from spins also within the imaging zone 108. The radio frequency coil 114 may contain multiple coil elements. The radio-frequency coil 114 is connected to a radio frequency transceiver 115. The radio-frequency coil 114 and radio frequency transceiver 115 may be replaced by separate transmit and receive coils and a separate transmitter and receiver. It is understood that the radio-frequency coil 114 and the radio frequency transceiver 115 are representative. The radio-frequency coil 114 is intended to also represent a dedicated transmit antenna and a dedicated receive antenna. Likewise, the transceiver 115 may also represent a separate transmitter and receivers. The radio-frequency coil 114 may also have multiple receive/transmit elements and the radio frequency transceiver 115 may have multiple receive/transmit channels.

The subject support 120 is attached to an optional actuator 122 that is able to move the subject support and the subject 118 through the imaging zone 108. In this way, a larger portion of the subject 118 or the entire subject 118 can be imaged. The transceiver 115, the magnetic field gradient coil power supply 112 and the actuator 122 are shown as being connected to a hardware interface 128 of computer system 126.

The computer 126 is further shown as containing a processor 130 which is operable for executing machine-readable instructions. The computer 126 is further shown as comprising a user interface 132, computer storage 134 and computer memory 136 which are all accessible and connected to the processor 130.

The computer memory 136 may also comprise a control module 143. The control module 152 may contain computer executable code or instructions, which enable the processor 130 to control the operation of the computer 126 as well as the magnetic resonance imaging system 100.

The computer memory 136 may contain one or more pulse sequences 141. The pulse sequences 141 are either instructions or data which can be converted into instructions which enable the processor 130 to acquire magnetic resonance data 140 using the magnetic resonance imaging system 100. For instance, the control module 143 may work in conjunction with the pulse sequences 141 to acquire the magnetic resonance imaging data 140.

For instance, the control module 143 may e.g. be configured to control the operation and function of the medical image data processing system 101. The computer system 126 is e.g. controlled by the control module 143 to process the medical image data 140, which may comprise reconstructing magnetic resonance images. These magnetic resonance images may be used as the medical image data 140 for the further data processing. The processing may comprise fitting an anatomical frame based on a segmentation and classifying tissue types of voxels.

For the processing of the medical image data 140, the computer memory 136 may further contain a segmentation module 144. The segmentation module 144 contains computer executable code or instructions which enable the processor 130 to perform a model-based segmentation of the medical image data 140. The result of the segmentation 160 comprises segmented medical image data which e.g. is stored in the computer storage 134.

The computer memory 136 may further contain a fitting module 146. The fitting module 146 contains computer executable code or instructions which enable the processor 130 to fit an anatomical frame of reference to the segmented medical image data 160. The resulting special encoded medical image data 162 may e.g. be stored in the computer storage 134.

The computer memory 136 may further contain a machine learning module 148. The machine learning module 148 contains computer executable code or instructions which enable the processor 130 to implement and execute a machine learning framework. The machine learning framework is trained to receive an image intensity and an anatomical position of a voxel as an input and to provide a tissue type classification of the voxel in response as an output. The output 164 machine learning module 148 may e.g. be stored in the computer storage 134.

The result of the classification 164 may e.g. be used by a transformation module 150. The transformation module 150 contains computer executable code or instructions which enable the processor 130 to transform MRI image data to pseudo-CT image data. The resulting pseudo-CT images 166 may e.g. be stored in the computer storage 134.

Figure 3:
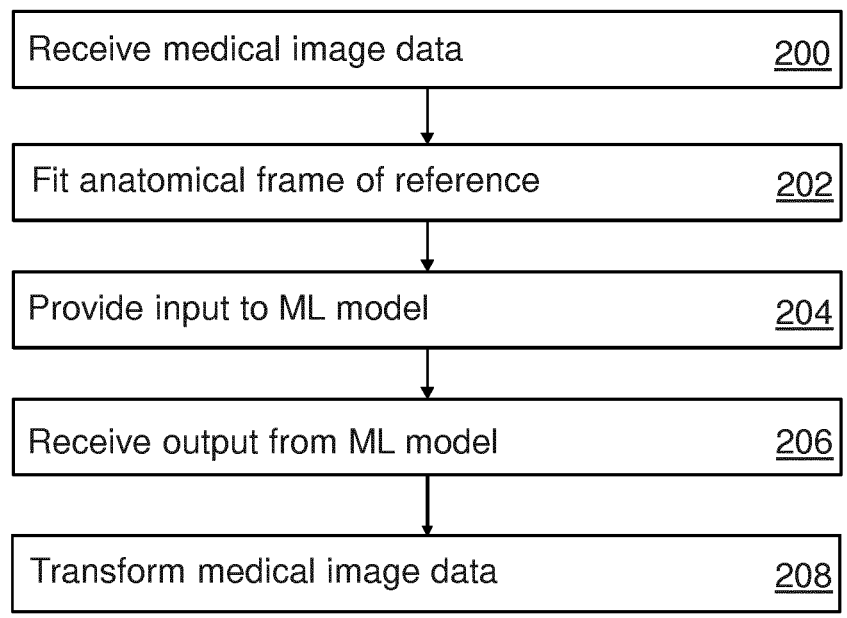
FIG. 3 illustrates an example of a method of operating the medical image data processing system.

FIG. 3 shows a schematic flowchart which illustrates a method of operating the medical image processing system of FIG. 1. In step 200, medical image data is received. The medical image data may e.g. be received from a local or a remote storage device. The received medical image data may for example be three-dimensional image data provided in form of a stack of two dimensional medical images. In step 202, an anatomical frame of reference to the medical image data using an anatomical reference structure. The fitting may e.g. comprise a model-based segmentation which comprises fitting a surface mesh to the surface of the anatomical structure of interest. The segmentation may e.g. indicate the contours of the anatomical structure of interest. The anatomical frame of reference is deformed with the surface mesh, when the deformed surface mesh is aligned with the anatomical structure of interest. In step 204, image intensities of the voxels as well as anatomical positions of the voxels with respect to the anatomical frame of reference are applied to the machine learning module as input. In step 206, the voxels are classified by the machine learning module and tissue types are provided as output of the machine learning module. In optional step 208, the information regarding the tissue type is used for transforming the medical image data in case of MRI data into pseudo-CT image data.

Figure 4:
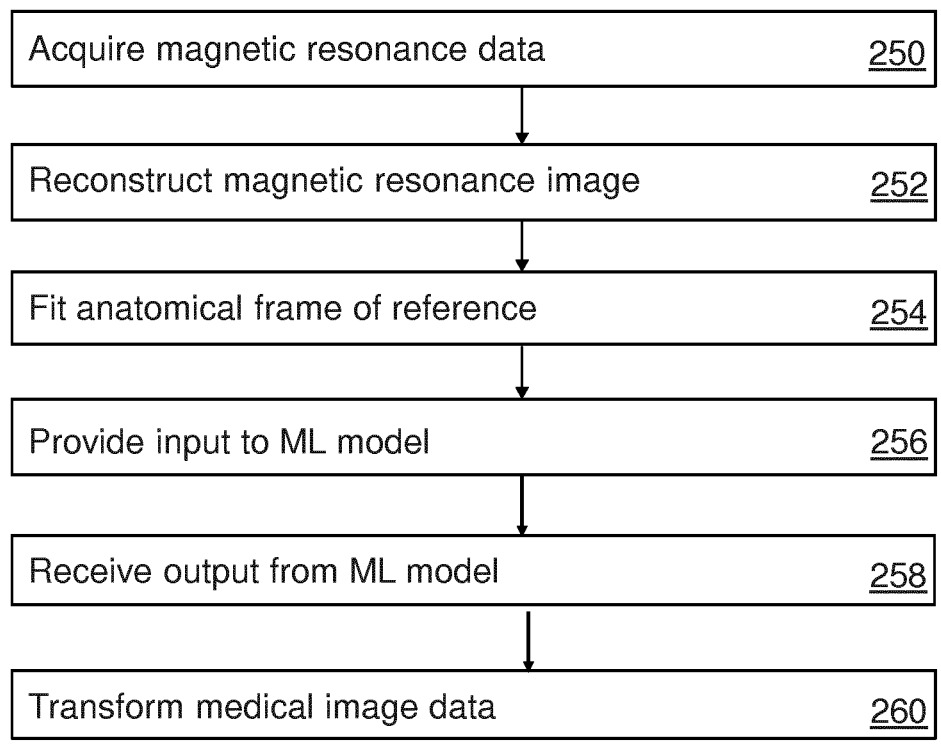
FIG. 4 illustrates an example of a method of operating the magnetic resonance imaging system.

FIG. 4 shows a schematic flowchart which illustrates a method of operating the medical image processing system and the magnetic resonance imaging system of FIG. 2. In step 250, magnetic resonance data is acquired using the magnetic resonance imaging system. In step 252, magnetic resonance images of an anatomical structure of interest are reconstructed using the acquired magnetic resonance data. Medical image data may thus be provided in form the reconstructed magnetic resonance images. Steps 254 to 260 may be identical with steps 202 to 208 of FIG. 3.

Figure 5:
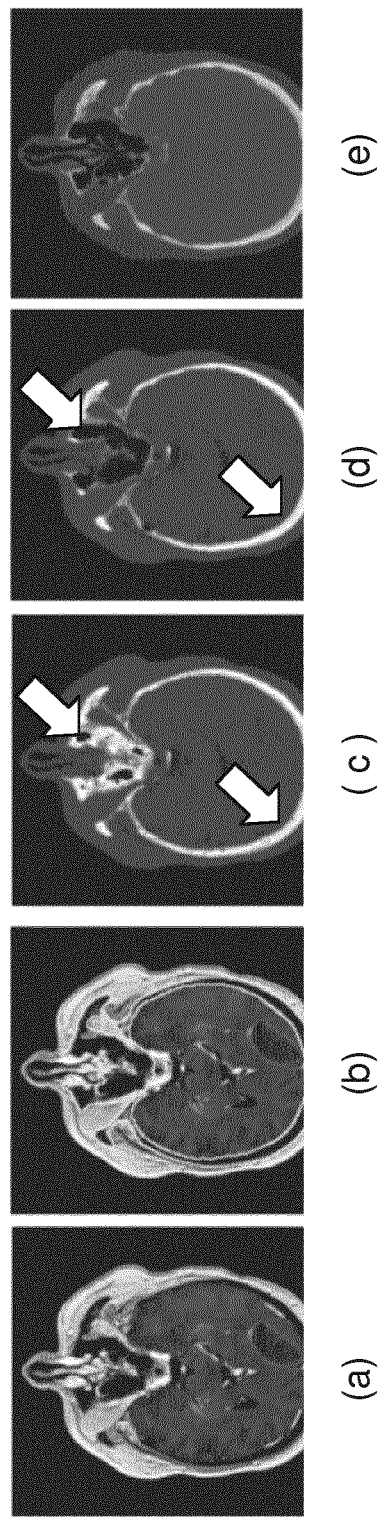
FIG. 5 illustrates an example of generating a pseudo-CT image.

FIG. 5 show a pseudo-CT image generated using MRI data acquired for an MR-only radiotherapy treatment planning. FIG. 5a shows an MR image reconstructed from acquired MRI data. FIG. 5b shows the MR image of FIG. 5a in combination with the result of a model-based segmentation. The mesh, more precisely the contours resulting from a 2D cut through the 3D mesh, provides information about the position of the underlying anatomy and may be used to deform an anatomical frame of reference assigned to the segmentation model as an anatomical reference structure onto the current MR image, i.e. spatial encoding. FIG. 5c shows a pseudo-CT image reconstructed form the MR image of FIG. 5a using an ML-based classification without spatial encoding and with additional image processing. Apparently, the nasal cavities cannot be distinguished from the skull since they both appear dark in FIG. 5a. FIG. 5d shows a pseudo-CT image generated form the MR image of FIG. 5a using an ML-based classification with spatial encoding and with additional image processing. Apparently, with spatial encoding dark MRI voxels can be separated into dark CT values representing air and bright CT values representing bone. FIG. 5e shows an actual CT image for comparison. Apparently, the result of the pseudo-CT image reconstruction taking into account spatial encoding as shown in FIG. 5d closely mimics the appearance of the actual CT image shown in FIG. 5e.

Figure 6:
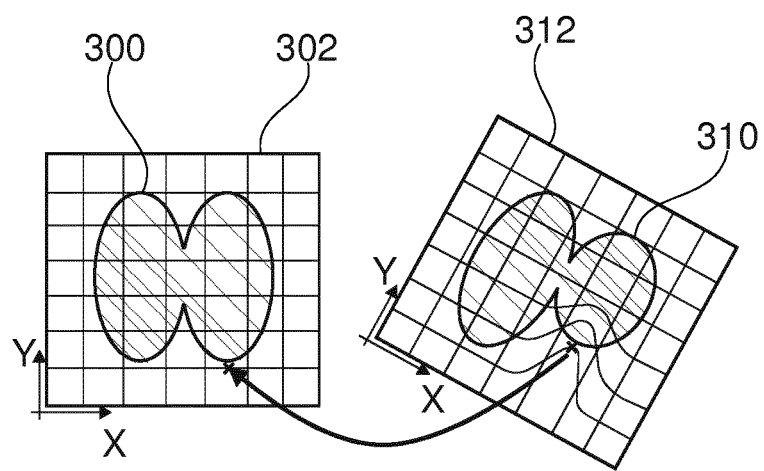
FIG. 6 illustrates an example of a fitting.

FIG. 6 shows an example for a fitting of an anatomical frame of reference 302 to an anatomical structure of reference. The anatomical frame of reference 302 is a spatial reference frame of a surface mesh 300 representing an anatomical reference structure. The coordinates defined by the anatomical frame of reference 302 are fixed relative to the surface mesh 300. Thus, when the surface mesh 300 is deformed in order to be aligned with the surface of the anatomical structure of interest, resulting in a deformed surface mesh 310, the anatomical frame of reference 302 is deformed as well, resulting in a deformed anatomical frame of reference 312. The coordinates defined by the deformed anatomical frame of reference 312 are assigned to the same anatomical position as the corresponding coordinates defined by the undeformed anatomical frame of reference 310. Thus, these coordinates may be used to effectively identify the anatomical potion of voxels comprised by the medical imaging data.

Figure 7:
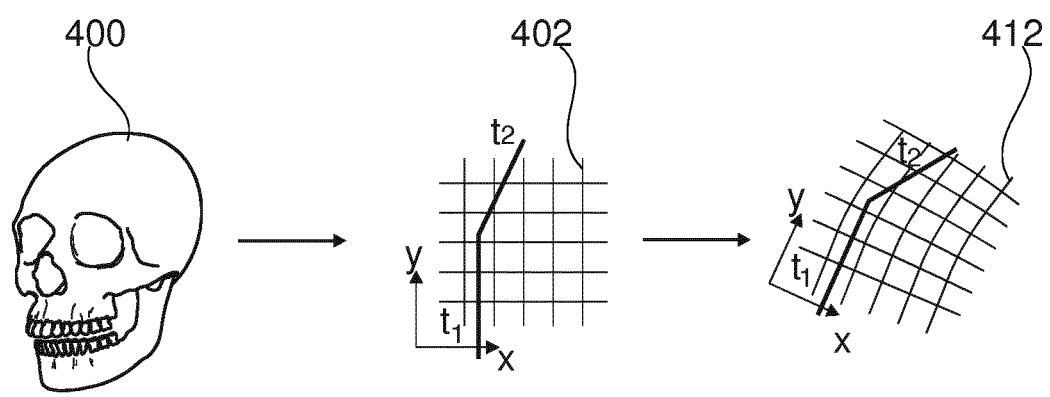
FIG. 7 illustrates an example of a fitting.

FIG. 7 shows a further example for a fitting of an anatomical frame of reference 402, resulting in a deformed anatomical frame of reference 412. For a model, like e.g. a surface mesh of a skull 400, an anatomical frame of reference 402 may be provided defining the spatial position of each point comprised by the surface area $t_1$, $t_2$ of the mesh 400. When the mesh 400 is deformed to segment a medical image, the anatomical frame of reference 402 is deformed as well resulting in the deformed anatomical frame of reference 412 which describes anatomical position relative to the deformed anatomical reference structure resulting from the deformation of mesh 400.

Figure 8:
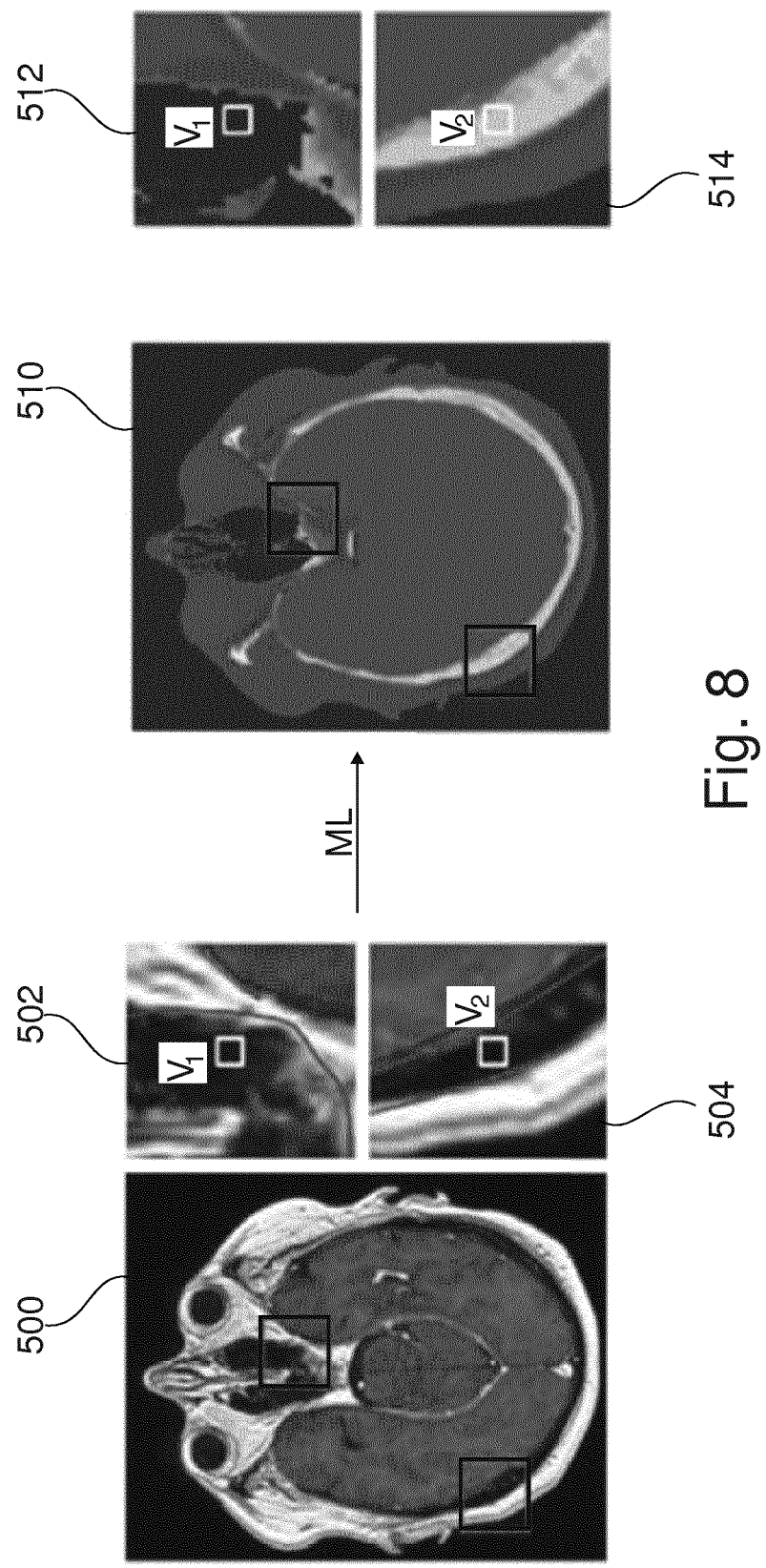
FIG. 8 illustrates an example of generating a pseudo-CT image.

FIG. 8 shows an example for transforming an MRI image 500 to a pseudo-CT image 510 using a machine learning framework which depends on the anatomical position of voxels of images 500, 510. As can be seen in the zoomed in images 502, 504, voxels v2 representing the bone of the skull (cf. image 504) and voxels v1 representing air in the nasal cavities (cf. image 502) are both dark and may not be distinguishable based on their image intensities. However, when applying a machine learning which depends on the anatomical position of voxels of image 500 in addition to the image intensity, bone and air represented by these voxels v1, v2 may be distinguished from each other. Thus, a highly accurate pseudo-CT image 510 may be generated using the MRI image 500. In the resulting pseudo-CT image 510, voxels representing bone v2 and voxels representing air v1 are clearly distinguished and the appropriate pseudo-CT image intensities are assigned to the same. This is illustrated in detail in zoom in images 512 and 514.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
101 medical image data processing system
104 main magnet
106 bore of magnet
108 imaging zone
110 magnetic field gradient coil
112 magnetic field gradient coil power supply
114 radio-frequency coil
115 transceiver
118 subject
120 subject support
122 actuator
125 database
126 computer
128 hardware interface
130 processor
132 user interface
134 computer storage
136 computer memory
140 medical image data
141 pule sequence commands
142 control module
143 control module
144 segmentation module
146 fitting module
148 machine learning module
150 transformation module
160 segmentation result
162 fitting result
164 machine learning result
166 pseudo-CT image
300 anatomical reference structure
302 anatomical frame of reference
310 deformed anatomical reference structure
312 deformed anatomical frame of reference
400 surface mesh
402 anatomical frame of reference
412 deformed anatomical frame of reference
500 MRI image
502 MRI image
504 MRI image
510 pseudo-CT image
512 pseudo-CT image
514 pseudo-CT image

The invention claimed is:

1. A medical image data processing system, the medical image data processing system comprising:
a memory storing machine executable instructions and a machine learning framework trained to receive an image intensity and an anatomical position of a voxel as an input and to provide a tissue type classification of the voxel in response as an output,
a processor for controlling the medical image data processing system, wherein execution of the machine executable instructions by the processor causes the processor to control the medical image data processing system to:
receive medical image data comprising an anatomical structure of interest,
fit an anatomical frame of reference to the medical image data using model-based segmentation, wherein a model used for the model-based segmentation comprises an anatomical reference structure in a reference space defined by the anatomical frame of reference, wherein the fitting of the anatomical frame of reference comprises deforming the reference space together with the anatomical reference structure to align the deformed anatomical reference structure with the anatomical structure of interest, wherein the fitting of the anatomical frame of reference provides anatomical positions relative to the deformed anatomical reference structure classify tissue types represented by voxels of the medical image data using the machine learning framework, wherein each voxel comprises an image intensity and wherein the image intensity and the anatomical positions of the voxels with respect to the deformed anatomical reference structure are used as the input to the machine learning framework.

2. The medical image data processing system of claim 1, wherein the medical image data comprises magnetic resonance image data.

3. The medical image data processing system of claim 2, wherein the medical image data processing system further comprises a magnetic resonance imaging system and wherein the magnetic resonance imaging system comprises:
a main magnet for generating a main magnetic field within an imaging zone,
a magnetic field gradient system for generating a spatially dependent gradient magnetic field within the imaging zone,
a radio-frequency antenna system configured for acquiring magnetic resonance data from the imaging zone,
wherein the memory further stores pulse sequence commands, wherein the pulse sequence commands are configured for controlling the magnetic resonance imaging system to acquire the magnetic resonance data from the imaging zone,
wherein the receiving of the medical image data comprises the execution of the machine executable instructions using pulse sequence commands and acquire the medical image data in form of magnetic resonance image data from the imaging zone by the radio-frequency antenna system.

4. The medical image data processing system of claim 2, wherein the execution of the machine executable instructions further causes the processor to generate a pseudo-CT image using the magnetic resonance image data and the classification result.

5. The medical image data processing system of claim 1, wherein the model used for the model-based segmentation comprises the anatomical reference structure in form of a surface mesh used for the segmentation.

6. The medical image data processing system of claim 5, wherein the model comprises the anatomical frame of reference in form of a spatial reference frame of the surface mesh and wherein the model-based segmentation comprises deforming the anatomical frame of reference together with the surface mesh.

7. The medical image data processing system of claim 1, wherein at least two voxels with identical image intensities are assigned to different classes representing different tissue types based on different anatomical positions of the voxels with respect to the anatomical frame of reference.

8. The medical image data processing system of claim 7, wherein a first one of the different classes represents bone and a second one of the different classes represents air.

9. The medical image data processing system of claim 1, wherein the receiving of the medical image data comprises: sending a request for the respective medical image data to a database comprising the medical image data, wherein in response to the request the requested medical image data is received from the database.

10. A method for controlling a medical image data processing system, the medical image data processing system comprising:
a memory storing machine executable instructions and a machine learning framework trained to receive an image intensity and an anatomical position of a voxel as an input and to provide a tissue type classification of the voxel in response as an output,
a processor for controlling the medical image data processing system, wherein execution of the machine executable instructions by the processor causes the processor to control the medical image data processing system to execute the method comprising:
receiving medical image data comprising an anatomical structure of interest,
fitting an anatomical frame of reference to the medical image data using model-based segmentation, wherein a model used for the model-based segmentation comprises an anatomical reference structure in a reference space defined by the anatomical frame of reference, wherein the fitting of the anatomical frame of reference comprises deforming the reference frame together with the anatomical reference structure to align the deformed anatomical reference structure with the anatomical structure of interest, wherein the fitting of the anatomical frame of reference provides anatomical positions relative to the deformed anatomical reference structure,
classifying tissue-types represented by voxels of the medical image data using the machine learning framework, wherein each voxel comprises an image intensity and wherein the anatomical positions of the voxels with respect to the deformed anatomical reference structure are used as the input to the machine learning framework.

11. The method of claim 10, wherein the medical image data processing system further comprises a magnetic resonance imaging system and wherein the magnetic resonance imaging system comprises:
a main magnet for generating a main magnetic field within an imaging zone,
a magnetic field gradient system for generating a spatially dependent gradient magnetic field within the imaging zone,
a radio-frequency antenna system configured for acquiring magnetic resonance data from the imaging zone,
wherein the memory further stores pulse sequence commands, wherein the pulse sequence commands are configured for controlling the magnetic resonance imaging system to acquire the magnetic resonance data from the imaging zone,
wherein the receiving of the medical image data comprises the execution of the machine executable instructions using pulse sequence commands and acquire the medical image data in form of magnetic resonance image data from the imaging zone by the radio-frequency antenna system.

12. A computer program product for controlling a medical image data processing system comprising machine executable instructions stored on a non-transitory computer readable medium for execution by a processor controlling the medical image processing system, wherein the medical image data processing system comprises a memory storing a machine learning framework trained to receive an image intensity and an anatomical position of a voxel as an input and to provide a tissue type classification of the voxel in response as an output and a processor for controlling the medical image data processing system, wherein execution of the machine executable instructions by the processor causes the processor to control the medical image data processing system to:

receive medical image data comprising an anatomical structure of interest, fit an anatomical frame of reference to the medical image data using model-based segmentation, wherein a model used for the model-based segmentation comprises an anatomical reference structure in a reference space defined by the anatomical frame of reference wherein the fitting of the anatomical frame of reference comprises deforming the reference space together with the anatomical reference structure to align the deformed anatomical reference structure with the anatomical structure of interest, wherein the fitting of the anatomical frame of reference provides anatomical positions relative to the deformed anatomical reference structure, classify tissue-types represented by voxels of the medical image data using a machine learning framework, wherein each voxel comprises an image intensity and wherein images intensities and the anatomical positions of the voxels with respect to the deformed anatomical reference structure are used as the input to the machine learning framework.

\* \* \* \* \*